(12) United States Patent
Pelivanov et al.

(10) Patent No.: US 10,126,273 B2
(45) Date of Patent: Nov. 13, 2018

(54) INSPECTION OF STRUCTURES

(71) Applicants: The Boeing Company, Chicago, IL (US); University of Washington, Seattle, WA (US)

(72) Inventors: Ivan Pelivanov, Seattle, WA (US); William P. Motzer, Charleston, SC (US); Matthew O'Donnell, Seattle, WA (US); Steven Kenneth Brady, Renton, WA (US); Gary Ernest Georgeson, Tacoma, WA (US); Jeffrey Reyner Kollgaard, Seattle, WA (US); Clarence Lavere Gordon, III, Renton, WA (US); Jill Paisley Bingham, Seattle, WA (US); Alan F. Stewart, Seattle, WA (US); James C. Kennedy, Summerville, SC (US)

(73) Assignee: The Boeing Company, Chicago, IL (US)

( * ) Notice: Subject to any disclaimer, the term of this patent is extended or adjusted under 35 U.S.C. 154(b) by 213 days.

(21) Appl. No.: 15/056,684

(22) Filed: Feb. 29, 2016

(65) Prior Publication Data

US 2017/0248551 A1   Aug. 31, 2017

(51) Int. Cl.
*G01N 29/04* (2006.01)
*G01N 29/22* (2006.01)
(Continued)

(52) U.S. Cl.
CPC .......... *G01N 29/07* (2013.01); *G01N 29/041* (2013.01); *G01N 29/043* (2013.01);
(Continued)

(58) Field of Classification Search
CPC .. G01N 29/2418; G01N 29/07; G01N 29/043; G01N 29/041; G01N 29/225; G01N 29/4445; G01N 2291/2694; G01N 2291/0289; G01N 2291/044; G01N 2291/011; G01N 2291/0231;
(Continued)

(56) References Cited

U.S. PATENT DOCUMENTS 5,790,620 A  *  8/1998  Okazaki  ............. B23K 26/0069
                                                                134/1
8,312,772 B2 * 11/2012  Tas ..................... G01N 21/1717
                                                                356/432
(Continued)

FOREIGN PATENT DOCUMENTS

KR          100822680 B1     4/2008
WO       WO2005070743 A1    8/2005

OTHER PUBLICATIONS

Extended European Search Report, dated Feb. 3, 2017, regarding Application No. 16200391.7, 8 pages.
(Continued)

*Primary Examiner* — J M Saint Surin
(74) *Attorney, Agent, or Firm* — Yee & Associates, P.C.

(57) ABSTRACT

A method of detecting inconsistencies in a structure is presented. A pulsed laser beam is directed towards the structure. A plurality of types of ultrasonic signals is formed in the structure when radiation of the pulsed laser beam is absorbed by the structure. The plurality of types of ultrasonic signals is detected to form data.

18 Claims, 9 Drawing Sheets

(51) Int. Cl.
*G01N 29/24* (2006.01)
*G01N 29/265* (2006.01)
*G01N 29/07* (2006.01)

(52) U.S. Cl.
CPC ....... *G01N 29/225* (2013.01); *G01N 29/2418* (2013.01); *G01N 29/265* (2013.01); *G01N 2291/011* (2013.01); *G01N 2291/0231* (2013.01); *G01N 2291/0232* (2013.01); *G01N 2291/0234* (2013.01); *G01N 2291/0235* (2013.01); *G01N 2291/0421* (2013.01); *G01N 2291/0422* (2013.01); *G01N 2291/0423* (2013.01); *G01N 2291/267* (2013.01); *G01N 2291/2694* (2013.01)

(58) Field of Classification Search
CPC ... G01N 2291/0232; G01N 2291/0234; G01N 2291/0235; G01N 2291/0421; G01N 2291/0422; G01N 2291/0423; G01N 2291/267
USPC .......................................................... 73/598
See application file for complete search history.

(56) References Cited

U.S. PATENT DOCUMENTS

| | | | |
|---|---|---|---|
| 8,368,289 B2 | 2/2013 | Karabutov et al. | |
| 9,164,066 B1 | 10/2015 | Bossi et al. | |
| 9,188,566 B2 | 11/2015 | Georgeson et al. | |
| 9,250,213 B1 | 2/2016 | Bossi et al. | |
| 2004/0003662 A1* | 1/2004 | Kenderian | G01N 29/12 73/579 |
| 2005/0023434 A1* | 2/2005 | Yacoubian | G01N 29/2418 250/200 |
| 2007/0163352 A1* | 7/2007 | Nielsen | B61K 9/10 73/668 |
| 2009/0199642 A1 | 8/2009 | Fukutomi et al. | |
| 2014/0116146 A1 | 5/2014 | Bossi et al. | |

OTHER PUBLICATIONS

Graham et al., "Laser Array/emat ultrasonic measurement of the penetration depths in a liquid weld pool," Transactions of the American Society of Mechanical Engineers, Series B:, Journal of Engineering for Industry, Asme, New York, vol. 122, Feb. 1, 2000, pp. 70-75.

Bossi et al., "Ultrasound Inspection System for Inspecting a Test Object with Non-Planar Features," U.S. Appl. No. 13/526,853, filed Jun. 19, 2012, 62 pages.

Pelivanov et al., "A kHz rate pump-probe scanner for advanced evaluation of aircraft composites," International Symposium on Laser Ultrasonics and Advanced Sensing, paper No. 12, Jun. 2015, 3 pages.

Pelivanov et al., "A new fiber-optic non-contact compact laser-ultrasound scanner for fast non-destructive testing and evaluation of aircraft composites," Journal of Applied Physics, vol. 115, Mar. 2014, 12 pages.

Pelivanov et al., "NDT of fiber-reinforced composites with a new fiber-optic pump-probe laser-ultrasound system," Photoacoustics, vol. 2, Jan. 2014, 13 pages.

European Examination Report, dated Jun. 26, 2018, regarding Application No. EP16200391.7, 7 pages.

* cited by examiner

INSPECTION OF STRUCTURES

BACKGROUND INFORMATION

1. Field

The present disclosure relates generally to non-destructive inspection and, in particular, to performing non-destructive inspection on a structure. Still more particularly, the present disclosure relates to a method and apparatus for detecting inconsistencies in a structure using a plurality of types of ultrasonic signals substantially simultaneously.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Non-destructive testing is commonly performed on these parts. Non-destructive testing is used to evaluate the properties of a part without altering the ability to use the part in service.

Ultrasound testing is a type of non-destructive testing. Ultrasound testing is often used to perform inspections on aircraft parts that include, or are comprised of, composite materials. Ultrasound testing involves transmitting acoustic waves through a test object, such as an aircraft part or structure.

Ultrasound testing is commonly performed using a transducer. The transducer is configured to send acoustic waves into a test object at a near side and detect a response to the acoustic waves. The response to these acoustic waves is analyzed to determine whether inconsistencies are present in the test object.

Different types of inconsistencies may be identified using different types of acoustic waves. For example, inconsistencies on a far side of a structure may be identified using shear waves. A far side of the structure is a side of the structure opposite the near side into which the acoustic waves are transmitted. As another example, inconsistencies on a near side of the structure may be identified using surface waves. In conventional ultrasonic inspection, each type of acoustic wave may be detected on a separate pass of the structure. For example, a first pass of the structure may detect surface waves while a second pass of the structure may detect shear waves. However, performing multiple inspection passes of the structure may use an undesirable amount of time, energy, or resources. Therefore, it would be desirable to have a method and apparatus that take into account at least some of the issues discussed above, as well as other possible issues.

SUMMARY

In one illustrative embodiment, a method of detecting inconsistencies in a structure is presented. A pulsed laser beam is directed towards the structure. A plurality of types of ultrasonic signals is formed in the structure when radiation of the pulsed laser beam is absorbed by the structure. The plurality of types of ultrasonic signals is detected using a single detector to form data.

In another illustrative embodiment, a method is presented. A pulsed laser beam is directed towards a structure. The pulsed laser beam is a line on a surface of the structure. A plurality of types of ultrasonic signals is formed in the structure when radiation of the pulsed laser beam is absorbed by the structure. The plurality of types of ultrasonic signals includes at least one of surface waves, shear waves, or longitudinal waves. The plurality of types of ultrasonic signals is detected by a single point detector to form data. An inconsistency is determined to be present in the structure using the data.

In a further illustrative embodiment, an apparatus is presented. The apparatus comprises a structure, a pulsed laser beam forming a line pump on a first surface of the structure, and a pulsed laser beam forming a point detector on the first surface of the structure.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that currently existing inspection techniques may have an undesirable level of precision. For example, existing inspection techniques may include contact or airborne ultrasonic probes or ultrasonic 'needle' probes. These existing detectors may have an undesirable level of precision for some structures. Further, some conventional single point inspection methods, such as x-ray diffraction, may not be suited to production or in-service inspection.

The illustrative embodiments further recognize and take into account that introduction of multiple types of waves into a structure during testing using traditional ultrasonic transducers would typically require multiple, physical transducers. There may not be enough physical space on an inspection system available for those transducers in the inspection region at one time, so multiple inspection passes would be required. Existing solutions can provide inspection of different types of inconsistencies, but not with a single inspection system or method. For example, far side inconsistencies or roughness or corrosion measurements may be detected using traditional ultrasound. However, each of these inconsistencies may not be detected with a single inspection system or method. A separate method would be needed to measure residual stress. For example, x-ray diffraction or surface wave ultrasound may be used to measure residual stresses.

The illustrative embodiments also recognize and take into account that it may be desirable to reduce cost for inspecting for inconsistencies such as joint inconsistencies, residual stress, corrosion thinning, manufacturing inconsistencies, or other types of inconsistencies. The illustrative embodiments also recognize and take into account that it may be desirable to ensure or improve safety by inspecting for inconsistencies such as joint inconsistencies, residual stress, corrosion thinning, manufacturing inconsistencies, or other types of inconsistencies.

Figure 1:
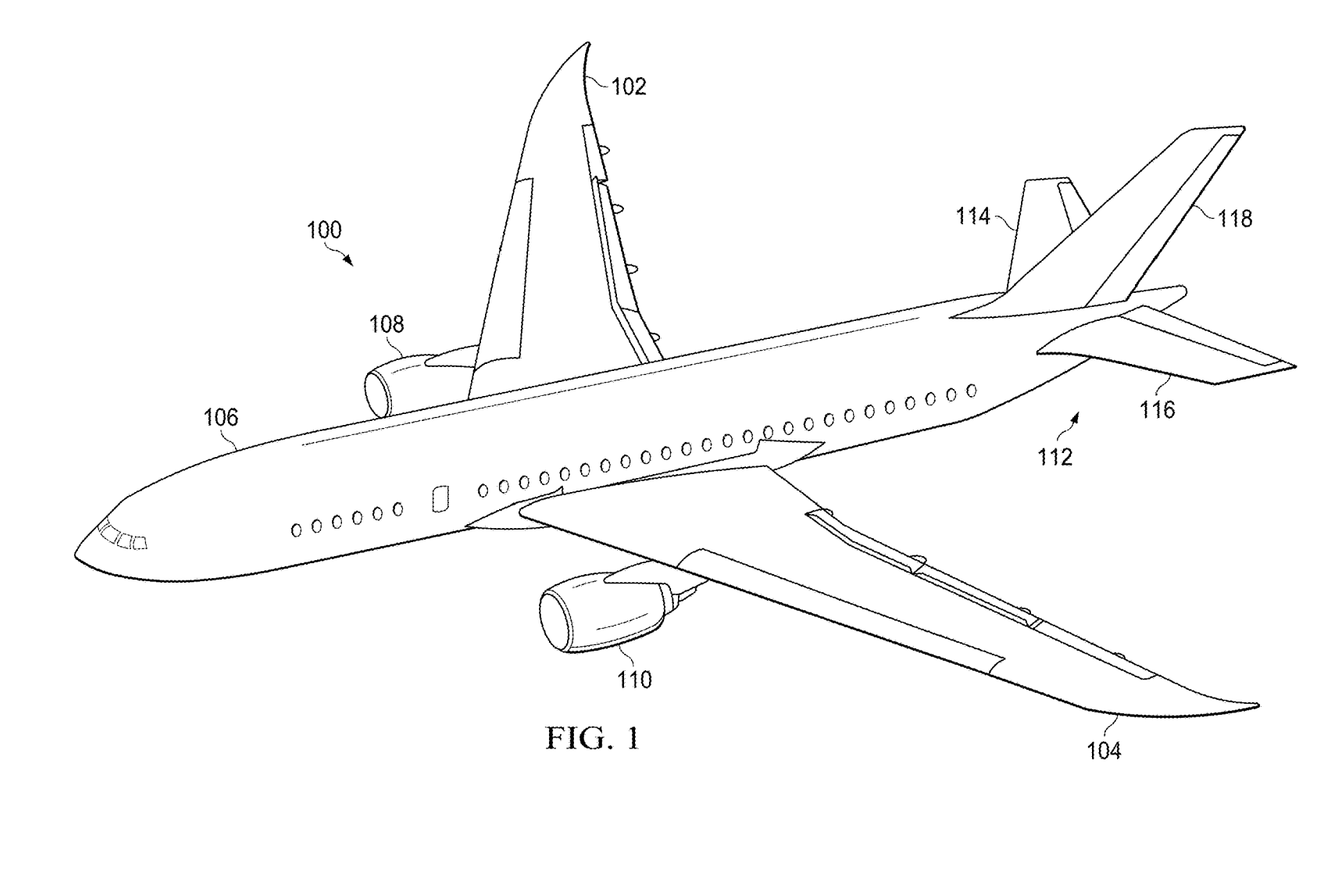
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106.

Aircraft 100 is an example of an aircraft having composite structures or structures formed of other materials that may be inspected with a laser ultrasound inspection system in accordance with an illustrative embodiment. For example, at least one of wing 102 or wing 104 may be inspected using a laser ultrasound inspection system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, although the structures may be formed of composite materials, a multi-modal inspection may be performed for any desirable type of material. For example, a plurality of waves may be used to inspect ceramics or metals.

Yet further, an illustrative embodiment may be applied to other types of structures. For example, structures other than platforms may be inspected for material changes using a laser ultrasound inspection system. Structures other than platforms may include medical devices, prosthetic limbs, or any other desirable products for the screening, diagnosis, treatment, or prevention or any combination or sub-combination thereof of physical or mental health conditions in human beings or animals.

Figure 2:
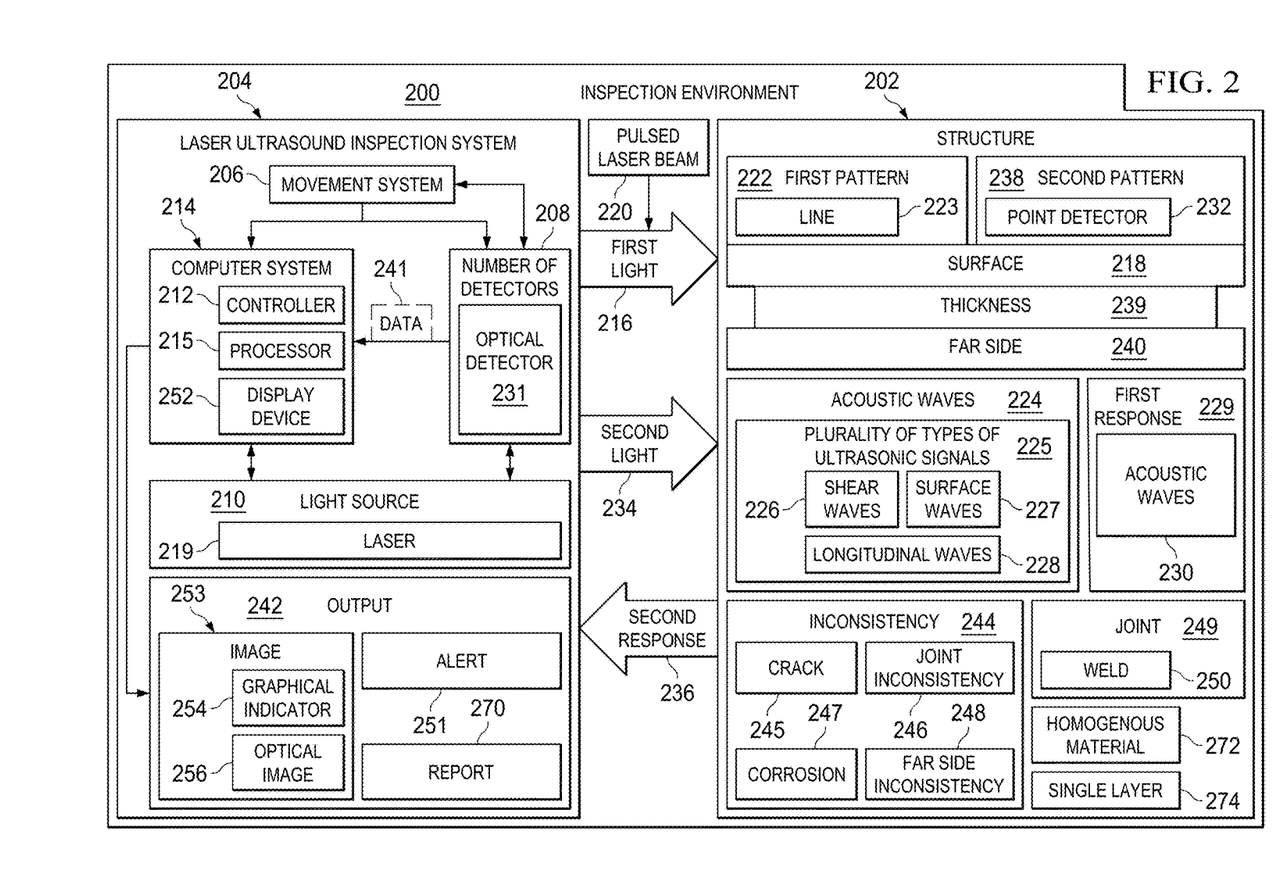
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. As depicted, inspection environment 200 includes structure 202. Structure 202 may take any number of forms. For example, structure 202 may be a part for an aircraft.

Structure 202 may be inspected using laser ultrasound inspection system 204. As depicted, laser ultrasound inspection system 204 includes movement system 206, number of detectors 208, light source 210, and controller 212.

In these illustrative examples, controller 212 controls the operation of laser ultrasound inspection system 204. Controller 212 may be implemented using hardware, software, firmware, or a combination thereof.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the controller may be implemented using, for example, without limitation, program code configured to run on a processor unit, such as processor 215. When firmware is used, the operations performed by the controller may be implemented using, for example, without limitation, program code and data stored in persistent memory to run on a processor unit.

When hardware is employed, the hardware may include one or more circuits that operate to perform the operations performed by the controller. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by the controller may be performed using organic components integrated with inorganic components. In some cases, the operations and/or processes may be performed by entirely organic components, excluding a human being. As one illustrative example, circuits in organic semiconductors may be used to perform these operations and/or processes.

Movement system 206 is configured to move light source 210 and number of detectors 208 relative to structure 202. Movement system 206 may be implemented using a number of different types of systems. For example, movement system 206 may be a robot. The robot may be, for example, a robotic arm that may move number of detectors 208 about a number of axes. Movement system 206 also may be, for example, without limitation, a gantry robot, a hand-operated scanning head, and other suitable types of movement systems.

Light source 210 is configured to transmit first light 216 onto surface 218 of structure 202. In some illustrative examples, light source 210 may be laser 219. More specifically, laser 219 may be a diode-pumped nanosecond laser.

When light source 210 takes the form of laser 219, first light 216 may be pulsed laser beam 220. In this illustrative example, first light 216 is transmitted in a manner that forms first pattern 222 on surface 218 of structure 202. In these illustrative examples, first pattern 222 of first light 216 is a plurality of areas on which first light 216 illuminates on surface 218. In some illustrative examples, first pattern 222 may take the form of line 223 on surface 218. When first pattern 222 takes the form of line 223, first light 216 has a width larger than its thickness, in order to create a linear impingement on surface 218 of structure 202.

When first light 216 takes the form of line 223 on surface 218, line 223 may be referred to as a line pump. "Pump" may be a term indicating laser-induced generation of a stress wave.

First light 216 is configured to form acoustic waves 224 within structure 202 when first light 216 encounters structure 202. Acoustic waves 224 may occur when first light 216 is transmitted onto surface 218 of structure 202. For example, energy in first light 216 may cause thermoelastic expansion in structure 202. The thermoelastic expansion may result in acoustic waves 224 in structure 202.

In these illustrative examples, acoustic waves 224 may be ultrasound sound waves. Thus, acoustic waves 224 may be ultrasonic signals. More specifically, acoustic waves 224 may take the form of wide-band ultrasonic signals. Acoustic waves 224 may have, for example, a frequency from about 20 kilohertz to about 100 megahertz depending on the particular implementation. The frequency for acoustic waves 224 may depend on the material used to form structure 202, the pulse width of the laser excitation, and other suitable factors.

Acoustic waves 224 may include a plurality of different types of waves. For example, acoustic waves 224 may take the form of plurality of types of ultrasonic signals 225. Plurality of types of ultrasonic signals 225 include at least one of shear waves 226, surface waves 227, or longitudinal waves 228.

Additionally, number of detectors 208 is configured to detect first response 229 to acoustic waves 224. First response 229 includes acoustic waves 230 that may occur as a result of scattering, reflection, modulation, and other changes to acoustic waves 224 traveling within structure 202. First response 229 is comprised of acoustic waves 230 that occur in response to acoustic waves 224. In this illustrative example, first response 229 is detected by number of detectors 208.

At least one of number of detectors 208 may take the form of optical detector 231. In some illustrative examples, at least one of number of detectors 208 may be point detector 232 formed on surface 218 of structure 202. In one example, number of detectors 208 may comprise any form of interferometer. For example, number of detectors 208 may include a fiber-optic modified Sagnac interferometer for non-contact detection of backscattered ultrasound. Number of detectors 208 may transmit second light 234 onto surface 218 of structure 202 and detect second response 236 to second light 234.

In one illustrative example, second light 234 also may be transmitted in the form of second pattern 238 onto surface 218 of structure 202. In this illustrative example, second pattern 238 may take the form of a point.

Second response 236 is second light 234 that has been deflected by first response 229 in this illustrative example. First response 229, caused by acoustic waves 224 traveling within structure 202, may reach surface 218 and may be detected. First response 229 may be detected using an interferometer that sends a reference light, such as second light 234 and detects the mechanical vibrations on surface 218 in second response 236. Number of detectors 208 may include any desirable form of interferometer.

Point detector 232 may be spaced apart from line 223 on surface 218 such that plurality of types of ultrasonic signals 225 may be detected. For example, point detector 232 may be spaced apart from line 223 on surface 218 such that plurality of types of ultrasonic signals 225 may be detected substantially simultaneously.

Shear waves 226 may move through thickness 239 of structure 202 at a diagonal. For example, shear waves 226 may move from surface 218 towards far side 240 of structure 202 at a diagonal. Shear waves 226 may then reflect from far side 240 of structure 202 towards surface 218.

Surface waves 227 may travel along surface 218 of structure 202. Surface waves 227 may not travel through thickness 239 of structure 202.

Longitudinal waves 228 may travel substantially perpendicular to surface 218 through thickness 239. For example, longitudinal waves 228 may move longitudinally from surface 218 to far side 240 and be reflected longitudinally back towards surface 218.

Number of detectors 208 sends data 241 to controller 212 when second response 236 is detected. Data 241 is used by controller 212 to generate output 242. Data 241 may include a full-bandwidth signal for a location of structure 202 being inspected. As laser ultrasound inspection system 204 is scanned across structure 202, data 241 for a plurality of locations on structure 202 is collected.

As depicted, output 242 may indicate whether inconsistency 244 is present in structure 202. Inconsistency 244 may be, for example, without limitation, crack 245, joint inconsistency 246, corrosion 247, or far side inconsistency 248. Far side inconsistency 248 may be on far side 240 of structure 202.

Data 241 representative of shear waves 226 may be used to identify far side inconsistency 248 or corrosion 247 on far side 240 of structure 202. Data 241 representative of surface waves 227 may be used to identify crack 245 or joint inconsistency 246. Joint inconsistency 246 may be present in joint 249. Joint 249 may join two components of structure 202. In some illustrative examples, joint 249 may take the form of weld 250. In these illustrative examples, joint inconsistency 246 may be an inconsistency in weld 250. In these illustrative examples, joint inconsistency 246 may result from the welding process.

Output 242 may take a number of different forms. For example, output 242 may take the form of alert 251. Alert 251 may indicate whether inconsistency 244 is present. Alert 251 may be displayed on display device 252 within computer system 214.

In another illustrative example, output 242 may be image 253. Image 253 also may be displayed on display device 252. Image 253 may be an image of a portion or all of structure 202 with graphical indicator 254 when inconsistency 244 is present in structure 202. Graphical indicator 254 may be displayed in a location in image 253 corresponding to a location in structure 202 where inconsistency 244 is detected. In other illustrative examples, if inconsistency 244 is absent, graphical indicator 254 may be displayed to indicate an absence of inconsistency 244.

In some illustrative examples, image 253 may be optical image 256. Optical image 256 may be an image of surface 218 of structure 202. In other illustrative examples, image 253 may be a representation of a portion of structure 202.

As still another illustrative example, output 242 may take the form of report 270. Report 270 may identify any inconsistencies in structure 202. Report 270 also may include other information, such as locations of inconsistencies, types of inconsistencies, sizes of inconsistencies, and other suitable types of information.

Structure 202 may be formed of any desirable material. Structure 202 may be formed of at least one of a composite, a metal, a ceramic, a polymeric material, a semi-conductor material, or a glass material.

In some illustrative examples, structure 202 is homogenous material 272. Homogeneous material 272 may be a uniform material with the same properties at each location of the material. However, structure 202 need not be formed of homogeneous material 272.

In some illustrative examples, structure 202 is single layer 274. By structure 202 being single layer 274, boundaries between multiple layers may not reflect or refract plurality of types of ultrasonic signals 225. For example, structure 202 may be a composite laminate formed of one type of composite material and forming single layer 274. When structure 202 is single layer 274, there are not any bonds or joints between surface 218 and far side 240.

The illustration of inspection environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although individual detectors are not depicted in laser ultrasound inspection system 204, laser ultrasound inspection system 204 may include any desirable quantity of detectors. For example, number of detectors 208 may include a first detector that detects second response 236 generated by shear waves 226 and surface waves 227, while a second detector detects second response 236 generated by longitudinal waves 228.

As another example, number of detectors 208 may comprise a plurality of receivers. In this example, number of detectors 208 may detect second response 236 generated by shear waves 226, surface waves 227, and longitudinal waves 228. In this example, second response 236 generated by shear waves 226 and surface waves 227 may be detected by a first receiver of number of detectors 208 while second response 236 generated by longitudinal waves 228 may be detected by a different receiver of number of detectors 208.

Further, inconsistency 244 may include any other type of inconsistencies. For example, although crack 245 is depicted as a possibility for inconsistency 244, inconsistency 244 may instead be any type of detectable near-surface inconsistency.

Figure 3:
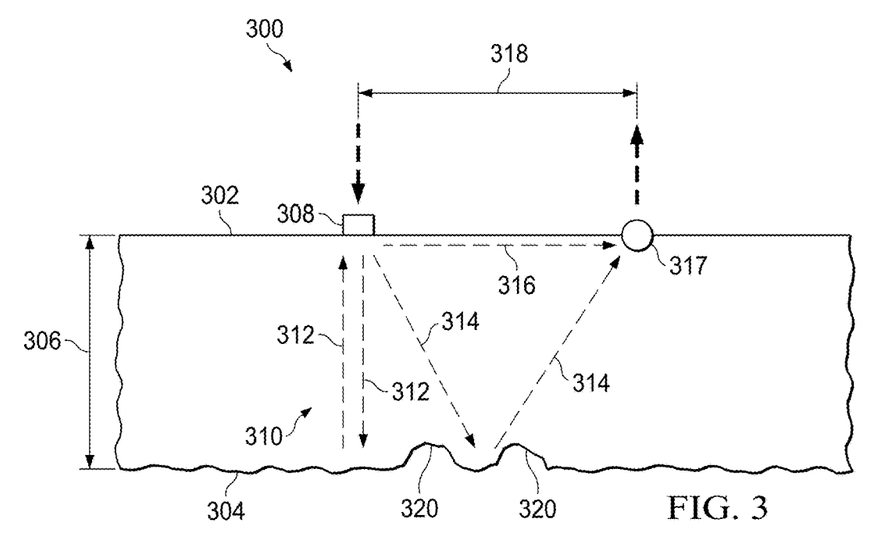
FIG. 3 is an illustration of a cross-section of a structure being inspected in accordance with an illustrative embodiment.

Turning now to FIG. 3, an illustration of a cross-section of a structure being inspected is depicted in accordance with an illustrative embodiment. Structure 300 may be a physical implementation of structure 202 of FIG. 2.

Structure 300 has surface 302, far side 304, and thickness 306. Line pump 308 may induce plurality of types of ultrasonic signals 310 in structure 300. Line pump 308 may be generated on surface 302 of structure 300 using a pulsed laser beam, such as pulsed laser beam 220 of FIG. 2. Plurality of types of ultrasonic signals 310 may include at least one of longitudinal waves 312, shear waves 314, and surface waves 316. In this illustrative example, shear waves 314 and surface waves 316 are detected by point detector 317 on surface 302. Line pump 308 and point detector 317 may be spaced distance 318 apart such that shear waves 314 and surface waves 316 may both be detected by point detector 317. Distance 318 may be changed for different structures. For example, distance 318 may be selected based on thickness 306.

As can be seen in FIG. 3, the size of point detector 317 is significantly smaller than distance 318. Due to at least one of the size or the location of point detector 317, multiple types of ultrasonic signals may be detected in a single pass of structure 300. For example, due to size of point detector 317, multiple receivers may be present.

Longitudinal waves 312 may be detected by a receiver positioned at substantially the same location as line pump 308. In some illustrative examples, point detector 317 and the receiver for longitudinal waves 312 may be different receivers of the same detector. In some illustrative examples, point detector 317 and the receiver for longitudinal waves 312 may be two different detectors. In each of the examples regardless of the quantity of detectors, longitudinal waves 312, shear waves 314, and surface waves 316 may be detected at substantially the same time.

In some illustrative examples, longitudinal waves 312, shear waves 314, and surface waves 316 may all be detected in the same "pass" of structure 300. However, due to the distances traveled by each of longitudinal waves 312, shear waves 314, and surface waves 316, at least one of longitudinal waves 312, shear waves 314, or surface waves 316 may be detected at a different time than another of longitudinal waves 312, shear waves 314, or surface waves 316.

Shear waves 314 may be used to detect inconsistencies 320 on far side 304 of structure 300. In this illustrative example, inconsistencies 320 take the form of pores on far side 304 of structure 300. More specifically, data representative of shear waves 314 sent from point detector 317 may be used to detect inconsistencies.

Surface waves 316 may be used to detect inconsistencies between line pump 308 and point detector 317. More specifically, data representative of surface waves 316 sent from point detector 317 may be used to detect inconsistencies. In this illustrative example, no inconsistencies are depicted between line pump 308 and point detector 317. Inconsistencies detected using surface waves 316 may be referred to as near surface inconsistencies.

Longitudinal waves 312 may be used to detect inconsistencies through thickness 306 of structure 300. More specifically, data representative of longitudinal waves 312 sent from a receiver positioned near line pump 308 may be used to detect inconsistencies. In this illustrative example, no inconsistencies are depicted through thickness 306 of structure 300 beneath line pump 308.

Figure 4:
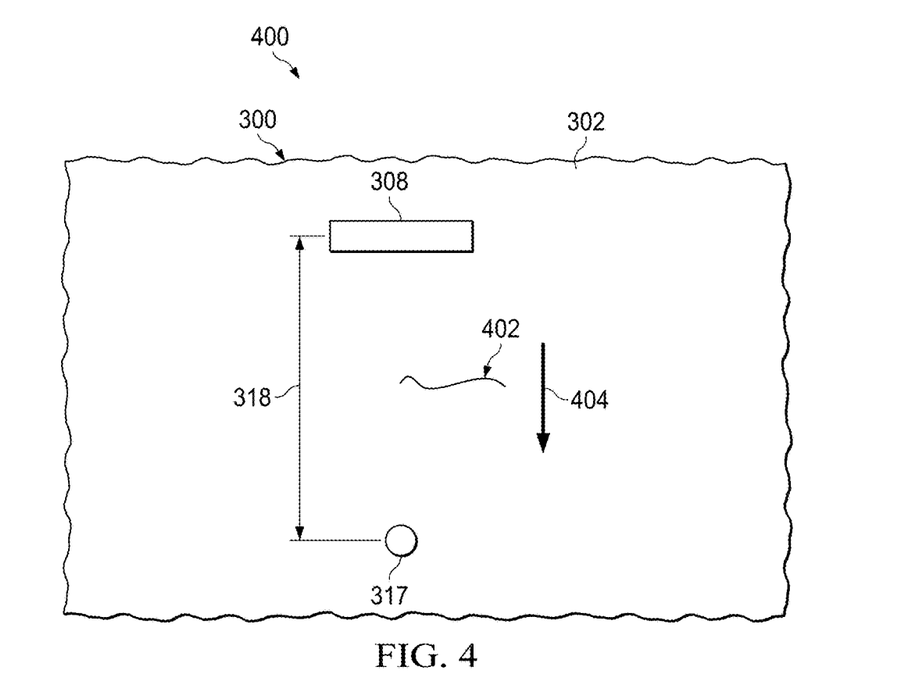
FIG. 4 is an illustration of an ultrasonic pump and probe in accordance with an illustrative embodiment.

Turning now to FIG. 4, an illustration of an ultrasonic pump and probe is depicted in accordance with an illustrative embodiment. View 400 may be a top view of surface 302 of structure 300 of FIG. 3.

In view 400, line pump 308 is visible on surface 302 of structure 300. In view 400, line pump 308 has a width larger than its thickness, in order to create a linear impingement on surface 302 of structure 300. Line pump 308 may be formed by directing a pulsed laser beam towards structure 300. As depicted, the pulsed laser beam is a line on surface 302 of structure 300.

In view 400, point detector 317 is visible on surface 302 of structure 300. As can be seen in view 400, point detector 317 is significantly smaller than distance 318 between line pump 308 and point detector 317.

In this illustrative example, structure 300 does not include a visible joint. However, as depicted, inconsistency 402 is present on surface 302 of structure 300. As depicted, inconsistency 402 may take the form of a crack. In other illustrative examples, inconsistency 402 may take the form of any surface or near surface inconsistency. In some illustrative examples, inconsistency 402 may not be visible to the eye.

During inspection of structure 300, shear waves 314 and surface waves 316 of FIG. 3 may travel in direction 404 from line pump 308 to point detector 317. To inspect multiple locations of structure 300, line pump 308 and point detector 317 may move in direction 404 along surface 302. Movement of line pump 308 and point detector 317 during inspection of structure 300 may be referred to as "scanning."

Figure 5:
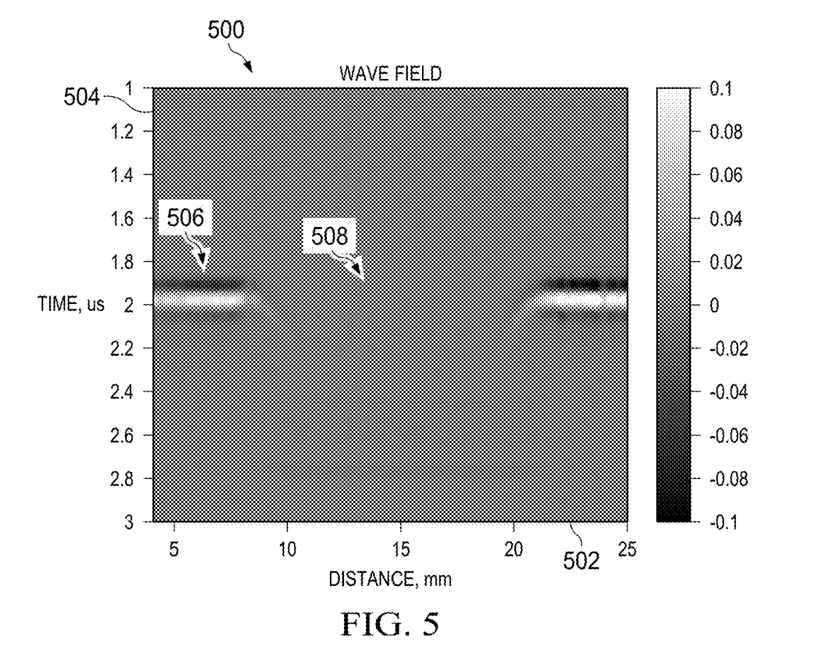
FIG. 5 is an illustration of a surface wavefield image in accordance with an illustrative embodiment.

Turning now to FIG. 5, an illustration of a surface wavefield image is depicted in accordance with an illustrative embodiment. Image 500 may be an example of image 253 of FIG. 2. Image 500 may be formed from data 241 of FIG. 2. Image 500 may be formed from data detected by point detector 317 of FIGS. 3 and 4. Image 500 may be formed from data representative of surface waves 316.

Image 500 has x-axis 502 of distance in millimeters and y-axis 504 of time in microseconds. In image 500, line 506 is visible. Break 508 in line 506 may be indicative of an inconsistency. In this illustrative example, break 508 may be indicative of inconsistency 402 of FIG. 4.

Figure 6:
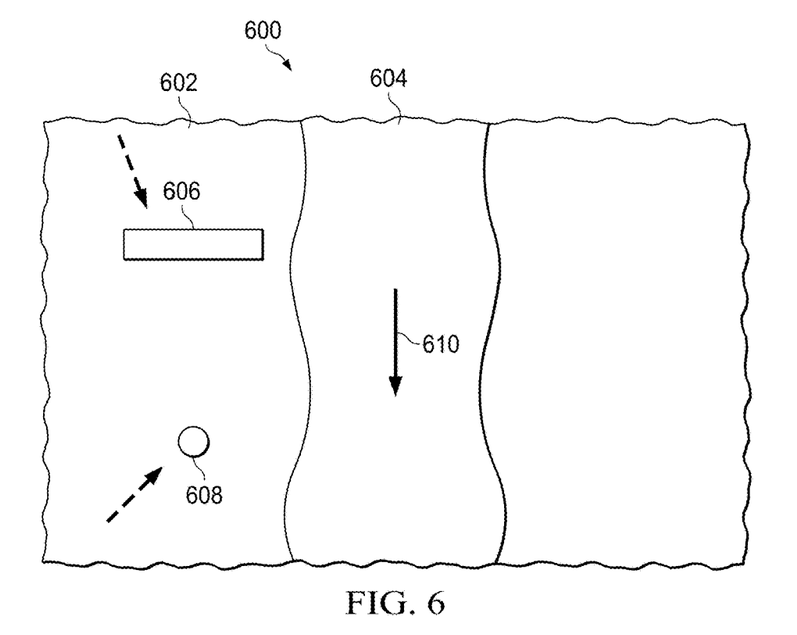
FIG. 6 is an illustration of an ultrasonic pump and probe positioned relative to a weld in accordance with an illustrative embodiment.

Turning now to FIG. 6, an illustration of an ultrasonic pump and probe positioned relative to a weld is depicted in accordance with an illustrative embodiment. View 600 may be a top view of surface 218 of structure 202 of FIG. 2.

View 600 depicts structure 602 having joint 604. In some illustrative examples, joint 604 may be a weld.

Line pump 606 may be a physical implementation of line 223 of FIG. 2. Point detector 608 may be a physical implementation of point detector 232. In some illustrative examples, line pump 606 may be the same as line pump 308 in FIG. 3. In some illustrative examples, point detector 608 may be the same as point detector 317 of FIG. 3.

To inspect joint 604, line pump 606 is set-up such that line pump 606 is perpendicular to direction 610 of joint 604. By positioning line pump 606 perpendicular to direction 610, ultrasonic signals may travel entirely through joint 604, when point detector 317 is positioned over joint 604.

In other illustrative examples, line pump 606 may be positioned parallel to direction 610. When line pump 606 is positioned parallel to direction 610, some inconsistencies may be more difficult to detect.

In some illustrative examples, the position of line pump 606 may be positioned based on the type of material of structure 602. For example, some materials for structure 602 may be anisotropic. An anisotropic material is direction dependent. As a result, changing the position of line pump 606 relative to structure 602 may also change the wave measurements from line pump 606.

In some illustrative examples, a material for structure 602 may be isotropic. Accordingly, wave measurements in structure 602 without inconsistencies may be isotropic. However, results for inconsistencies in structure 602 may be anisotropic. For example, wave measurements for an inconsistency in structure 602 may be anisotropic. For example, a wave speed may be dependent on the direction of line pump 606 when an inconsistency is present.

Accordingly, a first inspection may be performed with a plurality of types of ultrasonic signals in a first direction. Afterwards, a second inspection may be performed with a plurality of types of ultrasonic signals in a second direction. In some illustrative examples, the first direction and the second direction may have a ninety degrees difference.

During operation, surface waves propagate from line pump 606 to point detector 608. Surface waves may be detected by point detector 608 and recorded. Shear wave measurements may be displayed in any desirable format. For example, surface wave measurements through joint 604 may be displayed in an amplitude versus arrival time graph.

The waveform recorded for propagation of the surface waves through a region of structure 602 outside of joint 604 may be compared to the waveform recorded for propagation of the surface waves through a region within joint 604. At least one of the amplitude or arrival time of the surface wave waveforms may be different for propagation through joint 604 compared to propagation outside joint 604. For example, surface wave waveforms within joint 604 may have a smaller amplitude than surface wave waveforms outside of joint 604. As another example, arrival time of the surface wave waveforms for propagation through joint 604 may be greater than the arrival time of surface wave waveforms for propagation outside of joint 604.

In another example, the surface wave measurements may be displayed in a graph for wave speed as a function of position. The wave speed may have any desirable measurements, including in m/sec. In some illustrative examples, the surface wave measurements may be for a one-dimensional (line) scan across joint 604. Joint 604 may be identified as a region with reduced surface wave wave speed. This graph may be an example of one line within image 253 of FIG. 2.

A quality of joint 604 may be estimated based on changes in the surface wave speed between the material outside joint 604 and that within joint 604. For example, the magnitude of surface wave speed differences through joint 604 may be compared to guidelines for joints of acceptable quality. If the magnitude of surface wave speed differences are outside the guidelines, the joint 604 may be identified as having undesirable quality.

Figure 7:
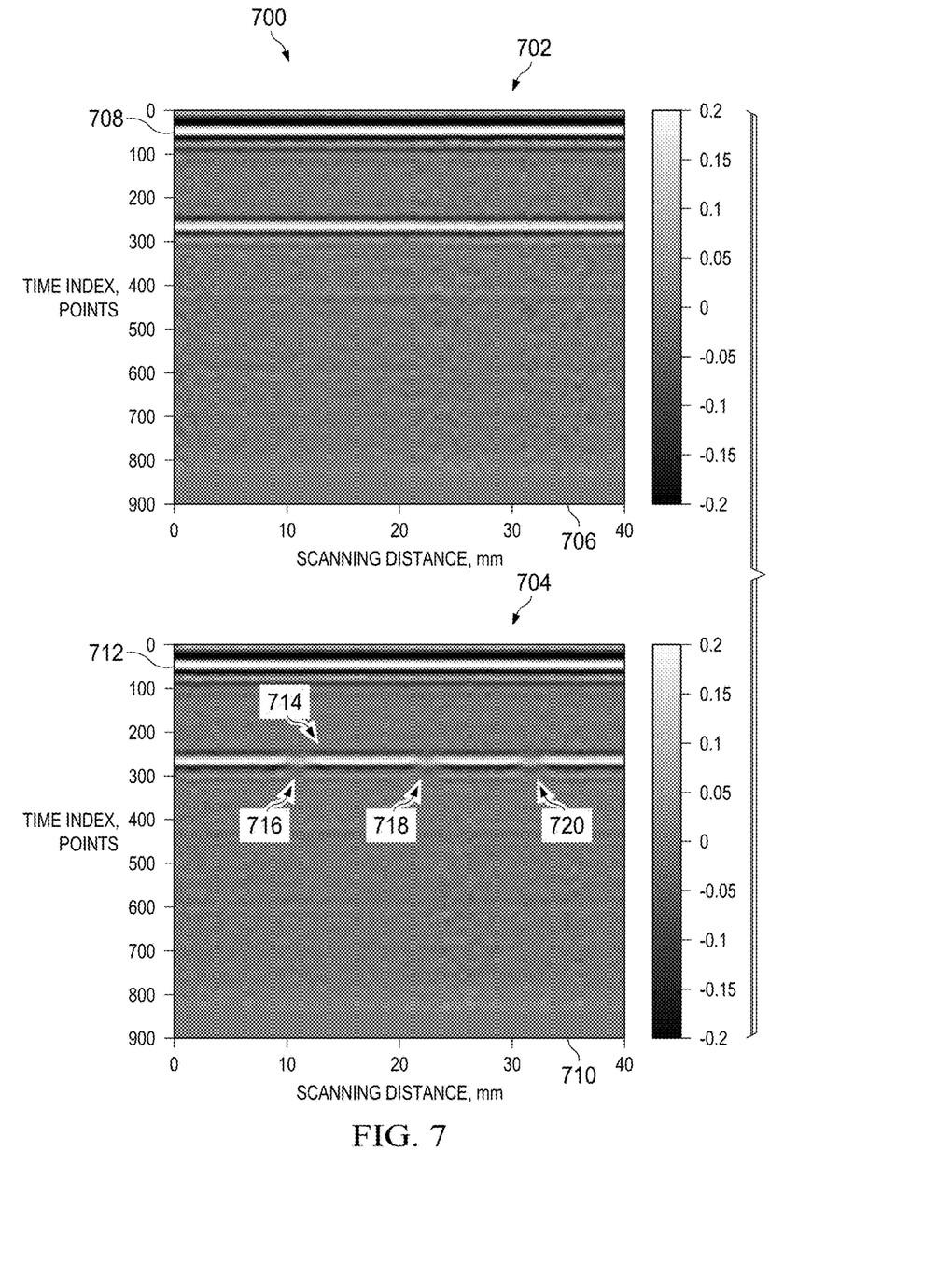
FIG. 7 is an illustration of two shear wavefield images in accordance with an illustrative embodiment.

Turning now to FIG. 7, an illustration of two shear wave wavefield images is depicted in accordance with an illustrative embodiment. View 700 depicts image 702 and image 704. Image 702 and image 704 may each be an example of image 253 of FIG. 2. Image 702 and image 704 may be formed from data 241 of FIG. 2. Image 702 and image 704 may be formed from data detected by point detector 317 of FIGS. 3 and 4. Image 702 and image 704 may be formed from data representative of shear waves 314.

Image 702 has x-axis 706 of scanning distance in millimeters. Image 702 has y-axis 708 of time index in points. Image 702 depicts data for a portion of a structure, such as structure 202 or structure 300 having a far side without any detected inconsistencies.

Image 704 has x-axis 710 of scanning distance in millimeters. Image 704 has y-axis 712 of time index in points. Image 704 depicts data for a portion of a structure, such as structure 202 or structure 300 having a far side with detected inconsistencies 714. Inconsistencies 714 may include inconsistency 716, inconsistency 718, and inconsistency 720. Inconsistencies 714 may include any type of detectable far side inconsistencies. For example, inconsistencies 714 may be at least one of corrosion, pores, or other types of inconsistencies. As depicted, the surface of the structure may not have any inconsistencies.

Figure 8:
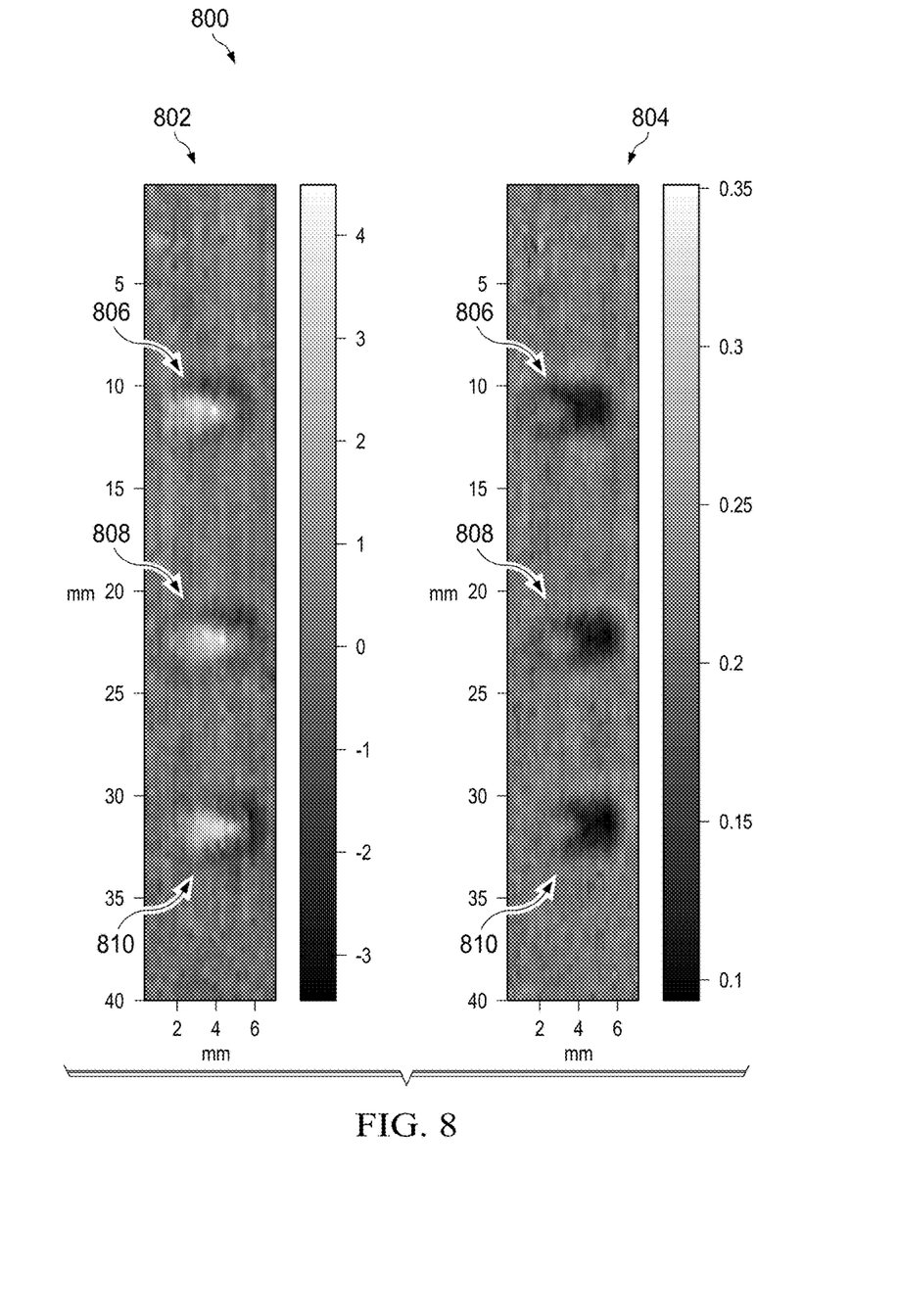
FIG. 8 is an illustration of ultrasonic C-scan images of a far side of a structure in accordance with an illustrative embodiment.

Turning now to FIG. 8, an illustration of ultrasonic C-scan images of a far side of a structure is depicted in accordance with an illustrative embodiment. View 800 depicts image 802 and image 804. Image 802 and image 804 may each be an example of image 253 of FIG. 2. Image 802 and image 804 may be formed from data 241 of FIG. 2. Image 802 and image 804 may be formed from data detected by point detector 317 and a point detector at line pump 308 of FIGS. 3 and 4. Image 802 and image 804 may be formed from data representative of shear waves 314.

Image 702 and image 704 of FIG. 7 may be further processed to produce clear images of inconsistencies within a structure. Both the arrival time and amplitude of the shear wave signal associated with reflections from a far side of the structure can be used to image the far side of the structure.

View 800 includes image 802 and image 804. Image 802 and image 804 depict a region of a structure having three inconsistencies on a far side of the structure. Image 802 and image 804 may be images of far side 304 of structure 300 of FIG. 3. Image 802 may be an arrival time image. Image 804 may be an amplitude image. Inconsistency 806, inconsistency 808, and inconsistency 810 may be observable in both image 802 and image 804. In some illustrative examples, inconsistency 806, inconsistency 808, and inconsistency 810 may be images of inconsistency 716, inconsistency 718, and inconsistency 720. Image 802 and image 804 demonstrate that inconsistencies on a far side of the structure may be visible in at least one of an arrival time image or an amplitude image.

The different components shown in FIG. 1 and FIGS. 3-8 may be combined with components in FIG. 2, used with components in FIG. 2, or a combination of the two. Additionally, some of the components in FIG. 1 and FIGS. 3-8 may be illustrative examples of how components shown in block form in FIG. 2 may be implemented as physical structures.

Figure 9:
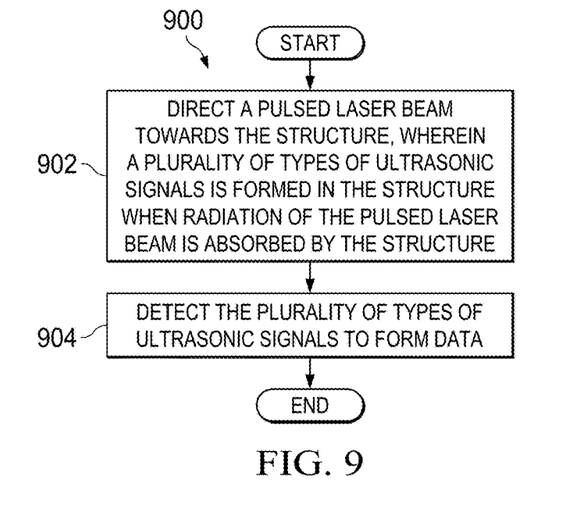
FIG. 9 is an illustration of a flowchart of a process for detecting inconsistencies in a structure in accordance with an illustrative embodiment.

Turning now to FIG. 9, an illustration of a flowchart of a process for detecting inconsistencies in a structure in accordance with an illustrative embodiment. The process illustrated in FIG. 9 may be implemented in an ultrasound inspection system such as laser ultrasound inspection system 204 in FIG. 2. The process illustrated in FIG. 9 may detect inconsistency 244 in structure 202 using data 241 formed by detecting plurality of types of ultrasonic signals 225.

Process 900 begins by directing a pulsed laser beam towards the structure, wherein a plurality of types of ultrasonic signals is formed in the structure when radiation of the pulsed laser beam is absorbed by the structure (operation 902). The plurality of types of ultrasonic signals may include at least one of shear waves, surface waves, or longitudinal waves. In some illustrative examples, the structure may include a joint. In these illustrative examples, the surface waves are transmitted through the joint in the structure. In some illustrative examples, the pulsed laser beam is a line on a surface of the structure.

Process 900 then detects the plurality of types of ultrasonic signals to form data (operation 904). Afterwards the process terminates. The plurality of types of ultrasonic signals may be detected by a number of detectors. In some illustrative examples, the plurality of types of ultrasonic signals may be detected by a single detector. In some illustrative examples, the plurality of types of ultrasonic signals is detected by a single point detector. In some illustrative examples, the pulsed laser beam and the single point detector are spaced apart such that the plurality of types of ultrasonic signals is detected.

In other illustrative examples, the number of detectors may include two detectors. The first detector may detect surface and shear waves while the second detector detects longitudinal waves.

In some illustrative examples, the structure is a homogenous material. In some illustrative examples, the structure may be formed of at least one of a composite, a metal, a ceramic, a polymeric material, or a glass material. In some illustrative examples, the structure is a single layer.

Figure 10:
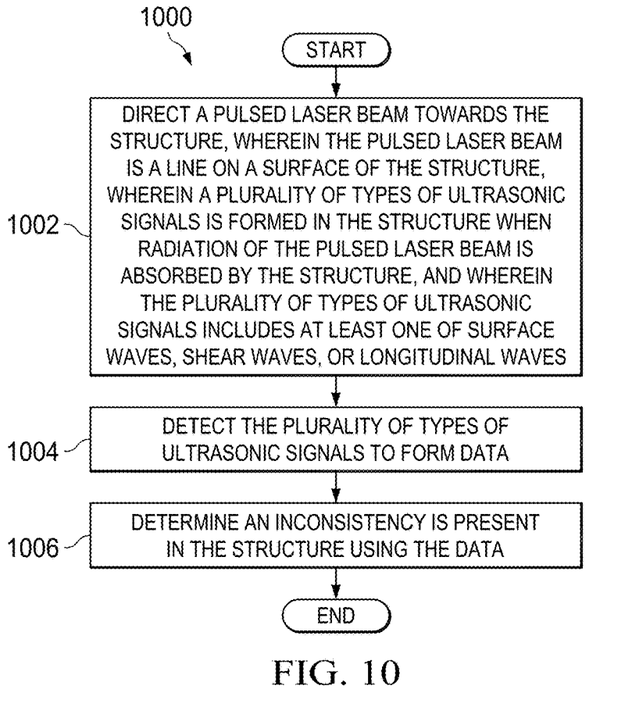
FIG. 10 is an illustration of a flowchart of a process for determining an inconsistency is present in a structure in accordance with an illustrative embodiment.

Turning now to FIG. 10, an illustration of a flowchart of a process for determining an inconsistency is present in a structure is depicted in accordance with an illustrative embodiment. The process illustrated in FIG. 10 may be implemented in an ultrasound inspection system such as laser ultrasound inspection system 204 in FIG. 2. The process illustrated in FIG. 10 may detect inconsistency 244 in structure 202 using data 241 formed by detecting plurality of types of ultrasonic signals 225.

Process 1000 may begin by directing a pulsed laser beam towards the structure, wherein the pulsed laser beam is a line on a surface of the structure, wherein a plurality of types of ultrasonic signals is formed in the structure when radiation of the pulsed laser beam is absorbed by the structure, and wherein the plurality of types of ultrasonic signals includes at least one of surface waves, shear waves, or longitudinal waves (operation 1002). In some examples, the structure is formed of a single layer.

Process 1000 may then detect the plurality of types of ultrasonic signals to form data (operation 1004). The plurality of types of ultrasonic signals may be detected by a number of detectors. In some illustrative examples, the plurality of types of ultrasonic signals may be detected by a single detector. In some illustrative examples, the plurality of types of ultrasonic signals is detected by a single point detector. In some illustrative examples, the pulsed laser beam and the single point detector are spaced apart such that the plurality of types of ultrasonic signals is detected.

In other illustrative examples, the number of detectors may include two detectors. The first detector may detect surface and shear waves while the second detector detects longitudinal waves.

Process 1000 then determines an inconsistency is present in the structure using the data (operation 1006). Afterwards the process terminates. In some illustrative examples, the inconsistency includes at least one of a joint inconsistency, corrosion, an inconsistency on a far side of the structure, or a crack.

In some illustrative examples, an inconsistency may be detected in the structure by comparing the data to reference data from a reference standard. The reference standard does not contain any inconsistencies. Differences between data and reference data may indicate the presence of an inconsistency in the structure.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, process 900 may further include identifying a crack in the structure using the data representing the surface waves. As another example, process 900 may include identifying corrosion in the structure using data representing the shear waves. As yet a further example, process 900 may also include identifying inconsistencies on a far side of the structure using the data representing the shear waves.

Figure 11:
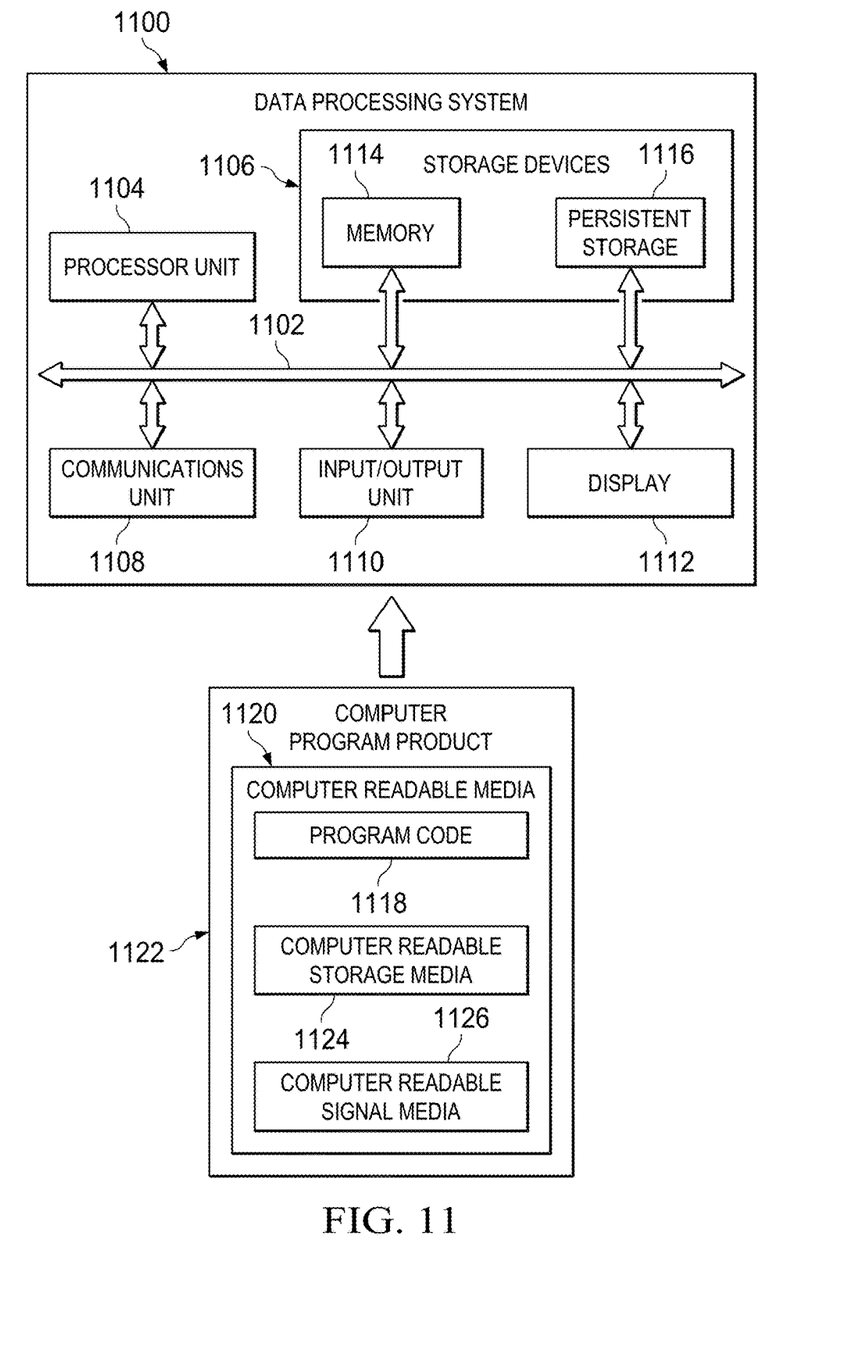
FIG. 11 is an illustration of a data processing system in the form of a block diagram in accordance with an illustrative embodiment.

Turning now to FIG. 11, an illustration of a data processing system in the form of a block diagram is depicted in accordance with an illustrative embodiment. Data processing system 1100 may be used to implement computer system 214 of FIG. 2. Data processing system 1100 may be used to process data as described in FIG. 3 and display output as depicted in FIGS. 4-8. As depicted, data processing system 1100 includes communications framework 1102, which provides communications between processor unit 1104, storage devices 1106, communications unit 1108, input/output unit 1110, and display 1112. In some cases, communications framework 1102 may be implemented as a bus system.

Processor unit 1104 is configured to execute instructions for software to perform a number of operations. Processor unit 1104 may comprise a number of processors, a multi-processor core, and/or some other type of processor, depending on the implementation. In some cases, processor unit 1104 may take the form of a hardware unit, such as a circuit system, an application specific integrated circuit (ASIC), a programmable logic device, or some other suitable type of hardware unit.

Instructions for the operating system, applications, and/or programs run by processor unit 1104 may be located in storage devices 1106. Storage devices 1106 may be in communication with processor unit 1104 through communications framework 1102. As used herein, a storage device, also referred to as a computer readable storage device, is any piece of hardware capable of storing information on a temporary and/or permanent basis. This information may include, but is not limited to, data, program code, and/or other information.

Memory 1114 and persistent storage 1116 are examples of storage devices 1106. Memory 1114 may take the form of, for example, a random access memory or some type of volatile or non-volatile storage device. Persistent storage 1116 may comprise any number of components or devices. For example, persistent storage 1116 may comprise a hard drive, a flash memory, a rewritable optical disk, a rewritable magnetic tape, or some combination of the above. The media used by persistent storage 1116 may or may not be removable.

Communications unit 1108 allows data processing system 1100 to communicate with other data processing systems and/or devices. Communications unit 1108 may provide communications using physical and/or wireless communications links.

Input/output unit 1110 allows input to be received from and output to be sent to other devices connected to data processing system 1100. For example, input/output unit 1110 may allow user input to be received through a keyboard, a mouse, and/or some other type of input device. As another example, input/output unit 1110 may allow output to be sent to a printer connected to data processing system 1100.

Display 1112 is configured to display information to a user. Display 1112 may comprise, for example, without limitation, a monitor, a touch screen, a laser display, a holographic display, a virtual display device, and/or some other type of display device.

In this illustrative example, the processes of the different illustrative embodiments may be performed by processor unit 1104 using computer-implemented instructions. These instructions may be referred to as program code, computer usable program code, or computer readable program code, and may be read and executed by one or more processors in processor unit 1104.

In these examples, program code 1118 is located in a functional form on computer readable media 1120, which is selectively removable, and may be loaded onto or transferred to data processing system 1100 for execution by processor unit 1104. Program code 1118 and computer readable media 1120 together form computer program product 1122. In this illustrative example, computer readable media 1120 may be computer readable storage media 1124 or computer readable signal media 1126.

Computer readable storage media 1124 is a physical or tangible storage device used to store program code 1118 rather than a medium that propagates or transmits program code 1118. Computer readable storage media 1124 may be, for example, without limitation, an optical or magnetic disk or a persistent storage device that is connected to data processing system 1100.

Alternatively, program code 1118 may be transferred to data processing system 1100 using computer readable signal media 1126. Computer readable signal media 1126 may be, for example, a propagated data signal containing program code 1118. This data signal may be an electromagnetic signal, an optical signal, and/or some other type of signal that can be transmitted over physical and/or wireless communications links.

The illustration of data processing system 1100 in FIG. 11 is not meant to provide architectural limitations to the manner in which the illustrative embodiments may be implemented. The different illustrative embodiments may be implemented in a data processing system that includes components in addition to or in place of those illustrated for data processing system 1100. Further, components shown in FIG. 11 may be varied from the illustrative examples shown.

Figure 12:
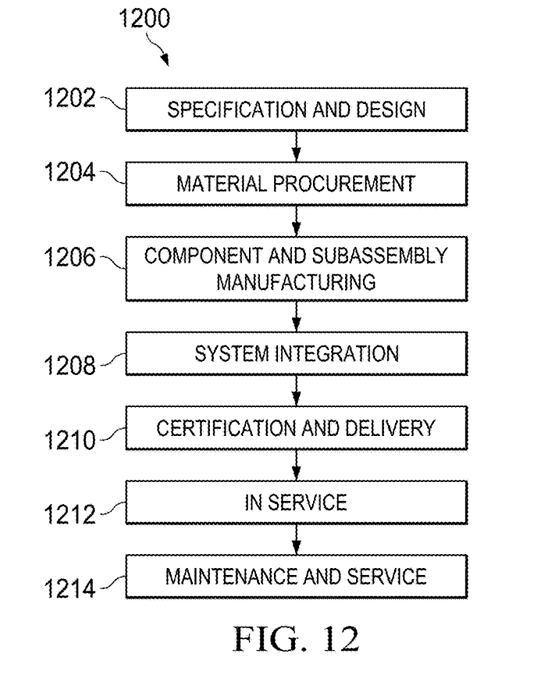
FIG. 12 is an illustration of an aircraft manufacturing and service method in the form of a block diagram in accordance with an illustrative embodiment.
Figure 13:
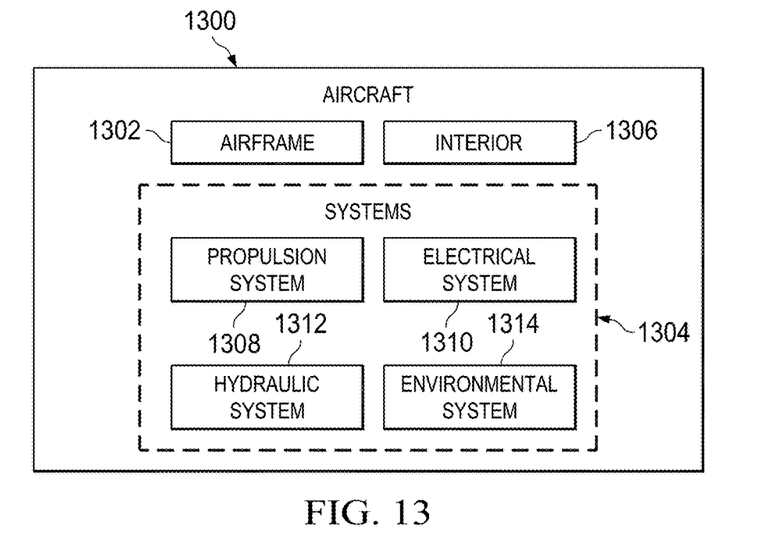
FIG. 13 is an illustration of an aircraft in the form of a block diagram, in which an illustrative embodiment may be implemented.

Illustrative embodiments of the disclosure may be described in the context of aircraft manufacturing and service method 1200, as shown in FIG. 12, and aircraft 1300, as shown in FIG. 13. Turning first to FIG. 12, an illustration of an aircraft manufacturing and service method is depicted in accordance with an illustrative embodiment. During preproduction, aircraft manufacturing and service method 1200 may include specification and design 1202 of aircraft 1300 and material procurement 1204.

During production, component and subassembly manufacturing 1206 and system integration 1208 of aircraft 1300 take place. Thereafter, aircraft 1300 may go through certification and delivery 1210 in order to be placed in service 1212. While in service 1212 by a customer, aircraft 1300 is scheduled for routine maintenance and service 1214, which may include modification, reconfiguration, refurbishment, and other maintenance or service.

Each of the processes of aircraft manufacturing and service method 1200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 13, an illustration of an aircraft is depicted in which an illustrative embodiment may be implemented. In this example, aircraft 1300 is produced by aircraft manufacturing and service method 1200 in FIG. 12, and may include airframe 1302 with plurality of systems 1304 and interior 1306. Examples of plurality of systems 1304 include one or more of propulsion system 1308, electrical system 1310, hydraulic system 1312, and environmental system 1314. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1200 in FIG. 12. One or more illustrative embodiments may be used during component and subassembly manufacturing 1206 in FIG. 12. For example, laser ultrasound inspection system 204 in FIG. 2 may be used to inspect structures during component and subassembly manufacturing 1206. Further, laser ultrasound inspection system 204 in FIG. 2 may be used to inspect an assembly during maintenance and service 1214 in FIG. 12. For example, structures of aircraft 1300 may be inspected during scheduled maintenance for aircraft 1300 using laser ultrasound inspection system 204.

Thus, one or more illustrative embodiments may provide a method and apparatus for determining if inconsistencies are present in a structure. Inconsistencies may be observable using conventional ultrasound techniques. However, inconsistencies through the thickness, near the surface, and on the far side of a structure may each require a separate inspection pass of the structure.

The illustrative embodiments may provide a method and apparatus for detecting inconsistencies using a plurality of types of ultrasonic signals substantially simultaneously. The illustrative embodiments may detect a plurality of types of ultrasonic signals substantially simultaneously. As a result, using the illustrative examples, the inspection time for the structure may be reduced.

The illustrative embodiments may reduce cost for inspecting for inconsistencies such as joint inconsistencies, residual stress, corrosion thinning, manufacturing inconsistencies, or other types of inconsistencies. The illustrative embodiments may ensure or improve safety by increasing ability to detect inconsistencies such as joint inconsistencies, residual stress, corrosion thinning, manufacturing inconsistencies, or other types of inconsistencies.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting inconsistencies in a structure, the method comprising:
    directing a pulsed laser beam towards the structure, wherein surface waves and shear waves are formed in the structure when radiation of the pulsed laser beam is absorbed by the structure; and
    detecting the surface waves and the shear waves at a point detector to form data, wherein the point detector is formed on a surface of the structure.

2. The method of claim 1, further comprising:
    identifying a crack in the structure using the data representing the surface waves.

3. The method of claim 1, wherein the surface waves are transmitted through a joint in the structure.

4. The method of claim 1, further comprising:
    identifying corrosion in the structure using data representing the shear waves.

5. The method of claim 1, further comprising:
    identifying inconsistencies on a far side of the structure using the data representing the shear waves.

6. The method of claim 1, wherein the pulsed laser beam and the point detector are spaced apart such that both the surface waves and shear waves are detected.

7. The method of claim 1, wherein the structure is a homogenous material.

8. The method of claim 1, wherein the structure is formed of at least one of a composite, a metal, a ceramic, a polymeric material, a semi-conductor material, or a glass material.

9. The method of claim 1, wherein the structure is a single layer.

10. The method of claim 1, wherein directing the pulsed laser beam towards the structure comprises positioning a line pump perpendicular to a direction of a joint such that ultrasonic signals travel entirely through the joint when the point detector is positioned over the joint.

11. The method of claim 1, wherein the point detector is significantly smaller than a distance between the pulsed laser beam and the point detector on the surface of the structure.

12. A method comprising:
    directing a pulsed laser beam towards a structure, wherein the pulsed laser beam is a line on a surface of the structure, wherein a plurality of types of ultrasonic signals is formed in the structure when radiation of the pulsed laser beam is absorbed by the structure, and wherein the plurality of types of ultrasonic signals includes surface waves and shear waves;

detecting the plurality of types of ultrasonic signals to form data, wherein the plurality of types of ultrasonic signals are detected using a single point detector formed by an interferometer, wherein the pulsed laser beam and a single point detector are spaced apart such that the plurality of types of ultrasonic signals is detected by the single point detector; and determining an inconsistency is present in the structure using the data.

13. The method of claim 12, wherein the structure is formed of a single layer.

14. The method of claim 12, wherein the inconsistency includes at least one of a joint inconsistency, corrosion, an inconsistency on a far side of the structure, or a crack.

15. The method of claim 12, wherein directing the pulsed laser beam towards the structure comprises positioning the line on the surface of the structure perpendicular to a direction of a joint such that ultrasonic signals travel entirely through the joint when the single point detector is positioned over the joint.

16. The method of claim 12, wherein the single point detector is significantly smaller than a distance between the pulsed laser beam and the single point detector on the surface of the structure.

17. An apparatus comprising:
a pulsed laser beam forming a line pump on a first surface of a structure; and
a pulsed laser beam forming a point detector on the first surface of the structure wherein the line pump and the point detector are spaced a distance apart, wherein the distance is selected such that the point detector detects surface waves and shear waves from the structure.

18. The apparatus of claim 17, wherein the pulsed laser beam forming the line pump is provided by laser ultrasonic equipment.

* * * * *